(12) United States Patent
Baraldi et al.

(10) Patent No.: US 7,919,624 B2
(45) Date of Patent: Apr. 5, 2011

(54) VR1 VANILLOID RECEPTOR ANTAGONISTS WITH A IONONIC SUBSTRUCTURE

(75) Inventors: Pier Giovanni Baraldi, Ferrara (IT);
Pier Andrea Borea, Ferrara (IT);
Pierangelo Geppetti, Ferrara (IT);
Maria Giovanna Pavani, Ferrara (IT);
Francesca Fruttarolo, Ferrara (IT);
Marcello Trevisani, Ferrara (IT)

(73) Assignee: Pharmeste S.R.L., Ferrara (IT)

( * ) Notice: Subject to any disclaimer, the term of this patent is extended or adjusted under 35 U.S.C. 154(b) by 51 days.

(21) Appl. No.: 12/307,919

(22) PCT Filed: Jul. 2, 2007

(86) PCT No.: PCT/EP2007/005844
§ 371 (c)(1),
(2), (4) Date: Sep. 16, 2009

(87) PCT Pub. No.: WO2008/006481
PCT Pub. Date: Jan. 17, 2008

(65) Prior Publication Data
US 2010/0035923 A1 Feb. 11, 2010

(30) Foreign Application Priority Data
Jul. 10, 2006 (EP) .................................. 06014299

(51) Int. Cl.
*C07D 217/00* (2006.01)
*A61K 31/472* (2006.01)
(52) U.S. Cl. ......................................... 546/139; 514/307
(58) Field of Classification Search .................. 514/307; 546/139
See application file for complete search history.

(56) References Cited

FOREIGN PATENT DOCUMENTS

| WO | 03/024920 | 3/2003 |
|----|-----------|--------|
| WO | 03/049702 | 6/2003 |
| WO | 2004/056774 | 7/2004 |

OTHER PUBLICATIONS

Doherty, Elizabeth M et al: "Discovery of potent, orally available vanilloid receptor-1 antagonists. Structure-activity relationship of N-aryl cinnamides," Journal of Medicinal Chemistry, vol. 48, No. 1, pp. 71-90, Jan. 13, 2005.
Gunthorpe M J et al: "Identification and characterization of SB-366791, a potent and selective vanilloid receptor (VR1/TRPV1) antagonist,"Neuropharmacology, Pergamon Press, Oxford, GB, vol. 46, No. 1, pp. 133-149, Jan. 2004.
Shimasake H et al: "Retinoidal dienamides and related aromatic amides. Replacement of the 9-ene structure of retinoic acid with a trans- or cis-amide group," Chemical and Pharmaceutical Bulletin 1995, Japan, vol. 43, No. 1, pp. 100-107, 1995.
PCT International Search Report for PCT/EP2007/005844 filed on Jul. 2, 2007 in the name of Pharmeste S.R.L.
PCT Written Opinion for PCT/EP2007/005844 filed on Jul. 2, 2007 in the name of Pharmeste S.R.L.
PCT International Preliminary Report on Patentability for PCT/EP2007/005844 filed on Jul. 2, 2007 in the name of Pharmeste S.R.L.
PCT International Search Report for PCT/EP2007/005835 filed on Jul. 2, 2007 in the name of Phameste S.R.L.
PCT Written Opinion for PCT/EP2007/005835 filed on Jul. 2, 2007 in the name of Phameste S.R.L.
Giovanni Appendino et al., "Clinically Useful Vanilloid Receptor RPVI Antagonists: Just around the Corner (or too Early to Tell)?", Progress in Medicinal Chemistry 2006, 44, 145-180.
Timor Baasov et al., "C-C Stretching Frequencies in Model Compounds of the Protonated Retinal Schiff Base", Angew. Chem. 1984, 23, 803-804.
P.G. Baraldi et al., "A Facile, Efficient of 2-substituted-4-Hydroxy-2-cyclopenten-1-ones", S. Synthesis 1986, 9, pp. 781-782.
Yoshihisa Kudo et al., "Monitoring of Intracellular Ca2+ Elevation in a Single Neural Cell Using a Fluorescence Microscope/Video-Camera System", Japan. J. Pharmacol. 41. 345-351 (1986).
Peter Meier et al, "Synthesis of Fonnylphenylpyridinecarboxylic Acids Using SuzukiMiyaura Coupling Reactions", Synthesis 2003, 4, pp. 551-554.
Peter J. Munson et al., "Ligand: A Versatile Computerized Approach for Characterization of Ligand-Binding Systems", Analytical Biochemistry 107, 220-239 (1980).
M. Nanasawa et al., "The Favorskii-type Rearrangement of 3-Bromo-b-ionone with Sodium Ethoxide", Bull. Chem. Soc. Jpn. 1982, 55, 3655-3656.
Michela Rigoni et al., "Neurogenic responses mediated by vanilloid receptor-I (TRPVI) are blocked by the high affinity antagonist, iodo-resiniferatoxin", British Journal of Pharmacology (2003) 138, 977-985.
Wen-Chung Shieh et al., "A Simple Asymmetric Synthesis of 4-Arylphenylalanines via Palladium-Catalyzed Cross-Coupling Reaction of Arylboronic Acids with Tyrosine Triflate", *J. Org. Chem.* 1992, 57, 379-381.
Arpad Szallasi et al., "[3H] resiniferatoxin binding by the vanilloid receptor: species-related differences, effects of temperature and sulfhydryl reagents", Naunyn-Schmiedeberg's Arch Pharmacol (1993) 347:84-91. Arpad Szallasi et al., "Resiniferatoxin", M. Neurosciences 1992, 8, 368.
Jidong Zhang et al., "A colored dendrimer as a new soluble support in organic synthesis. Part 1: Suzuki reaction", Tetrahedron Letters 42 (2001) 6683-6686.

*Primary Examiner* — Shailendra Kumar
(74) *Attorney, Agent, or Firm* — Steinfl & Bruno LLP

(57) ABSTRACT

The invention provides compounds of formula (I), wherein Y, R, n and X are as defined in the description, a process for their preparation and pharmaceutical compositions containing them. The compounds of formula (I) inhibit the Transient Receptor Potential Vanilloid 1 (TRPV1), which plays a pivotal role in the development of post-inflammatory analgesia, therefore they can be used as analgesic and anti-inflammatory drugs.

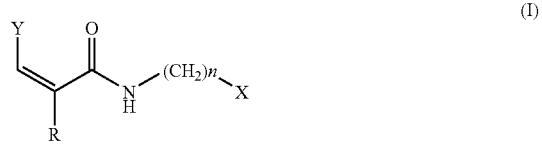

(I)

27 Claims, No Drawings

VR1 VANILLOID RECEPTOR ANTAGONISTS WITH A IONONIC SUBSTRUCTURE

CROSS REFERENCE TO RELATED APPLICATIONS

This application is the national phase of International Application PCT/EP20074/005844 filed on Jul. 2, 2007 which, in turn, claims priority to European Patent Application 06014299.9 filed on Jul. 10, 2006.

FIELD OF THE INVENTION

The present invention relates to antagonists of the vanilloid receptor, in particular to TRPV1 antagonists.

BACKGROUND OF THE INVENTION

The Transient Receptor Potential Vanilloid 1 (TRPV1) plays a pivotal role in the development of post-inflammatory hyperalgesia; thus, TRPV1 ligands could be clinically useful as analgesic and anti-inflammatory drugs.

Compounds deriving from natural products and referred to as capsaicinoids and resiniferonoids are known TRPV1 ligands. Among them, retvanil, the vanillamide of retinoic acid, is a potent agonist[1]

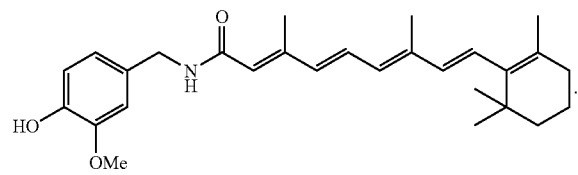

Ber. der Deutschen Chem. Gesellschaft, vol. 70, pp. 1009-1012 discloses the synthesis of the following compounds:

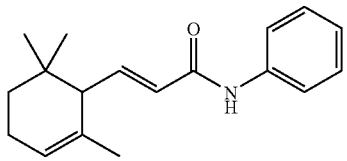

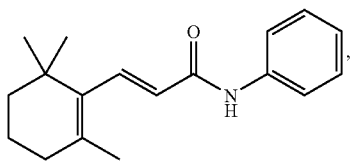

but it does not mention their biological properties.

WO 03/024920 mentions the use of retinoids for the treatment of arthritis and inflammatory dermatological disorders.

Chem. Pharm. Bull. 43(1) 100-107 (1995) discloses, in particular, the following compounds:

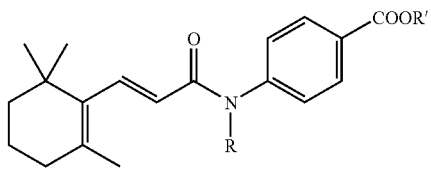

wherein R is hydrogen and R' is hydrogen or methyl and their retinoidal activity.

WO 03/049702, JOC vol. 48, no. 1, 2005, pp. 71-90 and Neuropharmacology, vol. 46, no. 1, 2004, pp. 133-149 disclose N-aryl cinnamides containing a moiety which can be represented as follows:

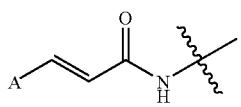

wherein A is substituted aryl. These compounds are antagonists of the vanilloid receptor and can be used for the treatment of a number of inflammatory conditions.

DESCRIPTION OF THE INVENTION

The present invention relates to TRPV1 inhibitors of formula (I)

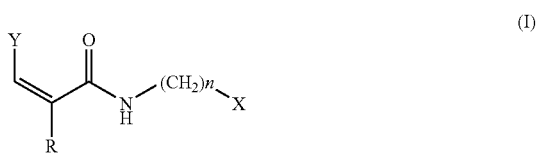

(I)

wherein:

Y is a group of formula:

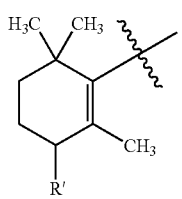

A

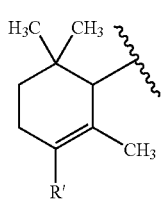

B

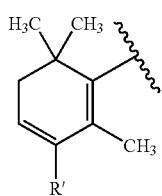

in which:
R' is selected from hydrogen, halogen, hydroxy, ($C_1$-$C_6$) alkyl, ($C_2$-$C_6$)alkenyl, ($C_3$-$C_6$)alkynyl, ($C_1$-$C_6$)alkoxy, ($C_1$-$C_6$)alkylamino, phenyl, naphthyl, phenoxy, naphthoxy, or phenylamino whose aromatic ring is optionally substituted with one or more halogen, hydroxy, ($C_1$-$C_4$) alkyl, ($C_1$-$C_4$)alkoxy and trifluoromethyl groups;
R is methyl or hydrogen;
n is 0 or 1;
X is selected from phenyl, pyridinyl, naphthyl, quinolinyl and isoquinolinyl, optionally substituted with one or more groups selected from halogen, hydroxy, ($C_1$-$C_4$) alkyl, ($C_1$-$C_4$)alkoxy and trifluoromethyl;
with the exclusion of the following compounds:

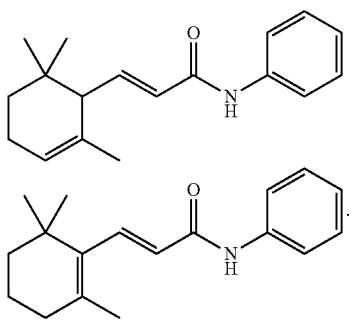

According to a first preferred embodiment, the invention relates to compounds of formula (I) wherein n is 0 and X is 5-isoquinolinyl. Among them, particularly preferred are the compounds wherein R is hydrogen and Y is a group of formula:

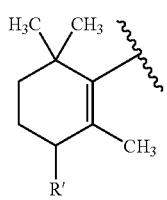

wherein R' is as defined above, more preferably hydrogen, methoxy or phenoxy optionally substituted as indicated above.

Examples of compounds of formula (I) are the following:
(2E)-N-(4-chlorophenyl)-3-(2,6,6-trimethylcyclohex-1-enyl)acrylamide;
(2E)-N-(4-chlorobenzyl)-3-(2,6,6-trimethylcyclohex-1-enyl)acrylamide;
(2E)-N-(isoquinolin-5-yl)-3-(2,6,6-trimethylcyclohex-1-enyl)acrylamide;
(2E)-N-(4-chlorophenyl)-3-(2,6,6-trimethylcyclohex-2-enyl)acrylamide;
(2E)-3-(2,6,6-trimethylcyclohex-1-enyl)-N-(naphthalen-1-yl)acrylamide;
(2E)-N-(4-chlorophenyl)-3-(2,6,6-trimethyl-3-phenoxycyclohex-1-enyl)acrylamide;
(2E)-N-(3-methoxyphenyl)-3-(2,6,6-trimethylcyclohex-1-enyl)acrylamide;
(2E)-N-(5-chloropyridin-2-yl)-3-(2,6,6-trimethylcyclohex-1-enyl)acrylamide;
(2E)-N-(4-chlorophenyl)-3-(2,6,6-trimethylcyclohexa-1,3-dienyl)acrylamide;
(2E)-N-(4-(trifluoromethyl)phenyl)-3-(2,6,6-trimethylcyclohex-1-enyl)acrylamide;
(2E)-3-(2,6,6-trimethylcyclohex-1-enyl)-N-(quinolin-3-yl)acrylamide;
(2E)-3-(2,6,6-trimethylcyclohex-1-enyl)-A-(quinolin-5-yl)acrylamide;
(2E)-N-(isoquinolin-5-yl)-3-(3-methoxy-2,6,6-trimethylcyclohex-1-enyl)acrylamide;
(2E)-N-(isoquinolin-5-yl)-3-(2,6,6-trimethyl-3-phenoxycyclohex-1-enyl)acrylamide;
(2E)-A-(isoquinolin-5-yl)-3-(3-(3-methoxyphenyl)-2,6,6-trimethylcyclohex-1-enyl)acrylamide;
(2E)-3-(3-(4-chlorophenoxy)-2,6,6-trimethylcyclohex-1-enyl)-N-(isoquinolin-5-yl)acrylamide;
(2E)-3-(3-(4-fluorophenoxy)-2,6,6-trimethylcyclohex-1-enyl)-N-(isoquinolin-5-yl)acrylamide;
(2E)-3-(3-(3-fluorophenoxy)-2,6,6-trimethylcyclohex-1-enyl)-N-(isoquinolin-5-yl)acrylamide;
(2E)-3-(3-(3,4-difluorophenoxy)-2,6,6-trimethylcyclohex-1-enyl)-N-(isoquinolin-5-yl)acrylamide.

The compounds of formula (I) can be prepared by means of conventional methods, such as the reaction of a compound of formula (II)

wherein Y and R are as defined above and the carboxy group is suitably activated to the amidation reaction with a commercially available compound of formula (III)

wherein X is as defined above.

The invention will be now illustrated by means of the following examples and schemes.

EXAMPLES

All commercially available compounds were purchased from Aldrich and were used without further purification. Reaction courses were monitored by thin-layer chromatography on silica gel (precoated $F_{254}$ Merck plates), the spots were examined with UV light and visualized with aqueous $KMnO_4$. Flash chromatography was performed using Merck silica gel (230-240 mesh). $^1$H-NMR spectra were recorded on Varian 400 MHz spectrometer using TMS as internal standard. Mass spectra were obtained with a Waters-Micromass ZMD spectrometer. Melting points were determined on a Buchi-Tottoli apparatus and are uncorrected.

Example 1

(2E)-N-(isoquinolin-5-yl)-3-(2,6,6-trimethylcyclohex-1-enyl)acrylamide Ia (Scheme 1)

The acid 1 was prepared from the commercially available β-ionone by haloformic reaction as described in the literature.[2] 1.0 mmol (194 mg) of acid 1 was dissolved in 8 ml of anhydrous DMF. EDCI (1.2 equiv., 1.2 mmol, 230 mg), HOBt (1.2 equiv., 1.2 mmol, 162 mg) and 5-aminoisoquinoline (1.2 equiv., 1.2 mmol, 173 mg) were added sequentially at 0° C. The reaction mixture was stirred at room temperature for 20 h. The solvent was evaporated under reduced pressure and the residue was dissolved in 50 ml of ethyl acetate. The organic phase was washed with water (2×20 ml), saturated sodium chloride solution (1×10 ml), dried over sodium sulphate and concentrated under vacuum. The crude residue was purified by column chromatography (silica gel, 3/7 ethyl acetate/hexane followed by ethyl acetate) and finally recrystallized from diethyl ether to give 150 mg of a beige solid. Yield=47%. Mp: (diethyl ether) 131-133° C. $^1$H NMR (CDCl$_3$, 400 MHz) δ 1.10 (6H, s), 1.49 (2H, m), 1.62 (2H, m), 1.81 (3H, s), 2.05 (2H, m), 6.18 (1H, d), 7.62 (2H, m), 7.70 (2H, m), 7.81 (1H, d), 8.38 (1H, bs), 8.53 (1H, d, J=5.6 Hz), 9.25 (1H, s); [M$^{+1}$] 321.7 (C$_{21}$H$_{24}$N$_2$O requires 320.43).

Example 2

(2E)-N-(isoquinolin-5-yl)-3-(3-methoxy-2,6,6-trimethylcyclohex-1-enyl)acrylamide Ib (Scheme 2)

Preparation 1
Synthesis of (2E)-methyl 3-(3-methoxy-2,6,6-trimethylcyclohex-1-enyl)acrylate 3[3]

A suspension of ester 2 (8 mmol, 1.66 g) and N-bromosuccinimide (1.1 equiv., 8.8 mmol, 1.56 g) in CCl$_4$ (30 ml) was refluxed for 1 h. After filtration through Celite, the solvent was evaporated. The residue was dissolved in MeOH (20 ml) and the reaction was refluxed overnight. The solvent was evaporated and the crude was dissolved in diethyl ether (30 ml) and washed with water (1×20 ml). The organic phase was dried over sodium sulfate and concentrated under vacuum. The purification of the crude residue by chromatographic column using 1/9 ethyl acetate/petroleum ether as eluant gave 715 mg of a colourless oil. Yield=37.5% (two steps). $^1$H NMR (CDCl$_3$, 400 MHz) δ 1.02 (3H, s), 1.04 (3H, s), 1.38 (2H, m), 1.62 (2H, m), 1.79 (3H, s), 3.37 (3H, s), 3.51 (1H, m), 3.75 (3H, s), 5.84 (1H, d, J=16 Hz), 7.33 (1H, d, J=16 Hz); [M$^{+1}$] 239.1 (C$_{14}$H$_{22}$O$_3$ requires 238.32).

Synthesis of (2E)-3-(3-methoxy-2,6,6-trimethylcyclohex-1-enyl)acrylic acid 4

LiOH (5 equiv., 630 mg) was added at 0° C. to a solution of ester 3 (3 mmol, 715 mg) in 3:1:1 THF/MeOH/water (15 ml) and the mixture was stirred at room temperature overnight. The solvents were removed under reduced pressure and the residue was diluted with water (20 ml). The acid was precipitated by addition of 10% HCl and then extracted with AcOEt (3×15 ml). The combined organic layers were dried over Na$_2$SO$_4$ and evaporated under vacuum to furnish 600 mg of an oily product. Yield=89%. $^1$H NMR (CDCl$_3$, 400 MHz) δ 1.03 (3H, s), 1.05 (3H, s), 1.39 (2H, m), 1.62 (2H, m), 1.80 (3H, s), 3.38 (3H, s), 3.52 (1H, m), 5.86 (1H, d, J=16 Hz), 7.45 (1H, d, J=16 Hz); [M$^{+1}$] 225.5 (C$_{13}$H$_{20}$O$_3$ requires 224.3).

Preparation 2
1.0 mmol (224 mg) of acid 4 was dissolved in 10 ml of anhydrous DMF. EDCI (1.2 equiv., 1.2 mmol, 230 mg), HOBt (1.2 equiv., 1.2 mmol, 162 mg) and 5-aminoisoquinoline (1.2 equiv., 1.2 mmol, 173 mg) were added sequentially at 0° C. The reaction mixture was stirred at room temperature for 20 h. The solvent was evaporated under reduced pressure and the residue was dissolved in 50 ml of ethyl acetate. The organic phase was washed with water (3×20 ml), and with saturated sodium chloride solution (1×10 ml), dried over sodium sulphate and concentrated under vacuum. The crude residue was purified by column chromatography (silica gel, ethyl acetate) and finally recrystallized from diethyl ether to give 160 mg of a yellow amorphous solid. Yield=45%. $^1$H NMR (CDCl$_3$, 400 MHz) δ 1.07 (6H, s), 1.42 (2H, m), 1.66 (2H, m), 1.86 (3H, s), 3.40 (3H, s) 3.48 (1H, m), 6.18 (1H, d), 7.51 (1H, m), 7.65 (3H, m), 7.84 (1H, d), 8.38 (1H, bs), 8.55 (1H, d, J=6 Hz), 9.26 (1H, s); [M$^{+1}$] 351.2 (C$_{22}$H$_{26}$N$_2$O$_2$ requires 350.45).

Example 3

(2E)-N-(isoquinolin-5-yl)-3-(2,6,6-trimethyl-3-phenoxycyclohex-1-enyl)acrylamide Ic (Scheme 3)

Preparation 1
Synthesis of (2E)-methyl 3-(2,6,6-trimethyl-3-phenoxycyclohex-1-enyl)acrylate 5c[4]

A suspension of ester 2 (3.12 mmol, 650 mg) and N-bromosuccinimide (1.1 equiv., 3.43 mmol, 611 mg) in CCl$_4$ (15 ml) was refluxed for 1 h. After filtration through Celite, the solvent was evaporated. The residue was dissolved in MeOH (5 ml) and added dropwise to a solution of sodium phenoxide (6.24 mmol) in methanol (10 ml). The resulting mixture was stirred overnight at room temperature. The reaction was poured into a cold 5% aqueous sodium hydroxide solution (15 ml) and the product was extracted with ether (2×20 ml). The organic layer was washed with water (1×10 ml), brine (1×5 ml), dried over anhydrous sodium sulfate and concentrated under vacuum. The purification of the crude by chromatographic column using 1/9 ethyl acetate/petroleum ether as eluant gave 350 mg of a colourless oil. Yield=37.5% (two steps). $^1$H NMR (CDCl$_3$, 400 MHz) δ 1.07 (3H, s), 1.12 (3H, s), 1.42 (2H, m), 1.78 (2H, m), 1.86 (3H, s), 3.78 (3H, s), 4.57 (1H, m), 5.92 (1H, d, J=16.4 Hz), 6.95 (3H, m), 7.29 (2H, m), 7.44 (1H, d, J=16.4 Hz); [M$^{+1}$] 301.2 (C$_{19}$H$_{24}$O$_3$ requires 300.39).

Synthesis of (2E)-3-(2,6,6-trimethyl-3-phenoxycyclohex-1-enyl)acrylic acid 6c

LiOH (5 equiv., 243 mg) was added at 0° C. to a solution of ester 5 (1.16 mmol, 350 mg) in 3:1:1 THF/MeOH/water (12.5 ml) and the mixture was stirred at room temperature overnight. The solvents were evaporated under reduced pressure and the residue was diluted with water (20 ml). The acid was precipitated by addition of 10% HCl and then extracted with AcOEt (3×15 ml). The combined organic layers were dried over Na$_2$SO$_4$ and evaporated under vacuum to furnish 300 mg of a white solid. Yield=90%. $^1$H NMR (CDCl$_3$, 400 MHz) δ 1.08 (3H, s), 1.13 (3H, s), 1.44 (2H, m), 1.78 (2H, m), 1.87 (3H, s), 4.58 (1H, m), 5.94 (1H, d, J=16.4 Hz), 6.96 (3H, m), 7.29 (2H, m), 7.52 (1H, d, J=16.4 Hz); [M$^{+1}$] 287.5 (C$_{18}$H$_{22}$O$_3$ requires 286.37).

Preparation 2
0.5 mmol (143 mg) of acid 6c were dissolved in 5 ml of anhydrous DMF. EDCI (1.2 equiv., 0.6 mmol, 115.2 mg), HOBt (1.2 equiv., 0.6 mmol, 81 mg) and 5-aminoisoquinoline (1.2 equiv., 0.6 mmol, 86.51 mg) were added sequentially at 0° C. The reaction mixture was stirred at room temperature for 20 h. The solvent was evaporated under reduced pressure and the residue was dissolved in 30 ml of ethyl acetate. The organic phase was washed with water (2×10 ml) and with a saturated sodium chloride solution (1×10 ml), dried over sodium sulphate and concentrated under vacuum. The crude solid was purified by column chromatography (silica gel, ethyl acetate/petroleum ether 8:2) and finally recrystallized from diethyl ether to give 100 mg of a white solid. Yield=48.5%. Mp: (diethyl ether) 141-143° C. $^1$H NMR (CDCl$_3$, 400 MHz) δ 1.14 (3H, s), 1.17 (3H, s), 1.47 (2H, m), 1.78 (2H, m), 1.95 (3H, s), 4.60 (1H, m), 6.41 (1H, d), 6.97 (2H, d, J=7.2 Hz), 7.26 (4H, m), 7.59 (1H, d, J=16 Hz), 7.80 (1H, t, J=8 Hz), 7.92 (1H, d, J=8 Hz), 8.17 (1H, m), 8.37 (1H, m), 8.52 (1H, bs), 9.26 (1H, s); [M$^{+1}$] 413.6 (C$_{27}$H$_{28}$N$_2$O$_2$ requires 412.52)

Example 4

(2E)-3-(3-(4-chlorophenoxy)-2,6,6-trimethylcyclo-hex-1-enyl)-N-(isoquinolin-5-yl)acrylamide Id (Scheme 3)

According to preparation 2 starting from 0.5 mmol of acid 6d 150 mg of compound Id was obtained as white solid. Yield=67%. Mp: (diethyl ether) 168° C. $^1$H NMR (CDCl$_3$, 400 MHz) δ 1.11 (3H, s), 1.14 (3H, s), 1.45 (2H, m), 1.66 (2H, m), 1.86 (3H, s), 4.76 (1H, m), 6.61 (1H, d), 7.06 (2H, d, J=8.8 Hz), 7.31 (2H, m), 7.34 (2H, d, J=8.8 Hz), 7.69 (1H, t, J=8 Hz), 7.95 (1H, d, J=8 Hz), 8.04 (1H, m), 8.27 (1H, bs), 8.58 (1H, d, J=6 Hz), 9.33 (1H, s); [M$^{+1}$] 448.4 (C$_{27}$H$_{27}$ClN$_2$O$_2$ requires 446.97).

Example 5

(2E)-3-(3-(4-fluorophenoxy)-2,6,6-trimethylcyclo-hex-1-enyl)-N-(isoquinolin-5-yl)acrylamide Ie (Scheme 3)

According to preparation 2 starting from 0.5 mmol of acid 6e 100 mg of compound Ie was obtained as white solid. Yield=46%. Mp: (diethyl ether) 135-137° C. $^1$H NMR (CDCl$_3$, 400 MHz) δ 1.11 (3H, s), 1.15 (3H, s), 1.44 (2H, m), 1.71 (2H, m), 1.92 (3H, s), 4.50 (1H, m), 6.21 (1H, d), 6.91 (2H, m), 6.98 (2H, m), 7.54 (1H, d, J=15.6 Hz), 7.72 (3H, m), 7.87 (1H, d), 8.41 (1H, bs), 8.55 (1H, d, J=6.4 Hz), 9.28 (1H, s); [M$^{+1}$] 431.6 (C$_{27}$H$_{27}$FN$_2$O$_2$ requires 430.51).

Example 6

(2E)-3-(3-(3-fluorophenoxy)-2,6,6-trimethylcyclo-hex-1-enyl)-N-(isoquinolin-5-yl)acrylamide If (Scheme 3)

According to preparation 2 starting from 0.5 mmol of acid 6f 90 mg of compound If was obtained as white solid. Yield=42%. Mp: (diethyl ether) 147° C. $^1$H NMR (CDCl$_3$, 200 MHz) δ 1.11 (3H, s), 1.14 (3H, s), 1.57 (2H, m), 1.71 (2H, m), 1.88 (3H, s), 4.56 (1H, m), 6.20 (1H, d), 6.70 (4H, m), 7.58 (1H, d, J=15.6 Hz), 7.65 (3H, m), 7.85 (1H, d), 8.38 (1H, bs), 8.59 (1H, d, J=5.8 Hz), 9.29 (1H, s); [M$^{+1}$] 431.5 (C$_{27}$H$_{27}$FN$_2$O$_2$ requires 430.51).

(2E)-3-(3-(3,4-difluorophenoxy)-2,6,6-trimethylcy-clohex-1-enyl)-N-(isoquinolin-5-yl)acrylamide Ig (Scheme 3)

According to preparation 2 starting from 0.5 mmol of acid 6g 90 mg of compound Ig was obtained as white solid. Yield=40%. Mp: (diethyl ether) 155° C. $^1$H NMR (CDCl$_3$, 200 MHz) δ 1.11 (3H, s), 1.14 (3H, s), 1.53 (2H, m), 1.75 (2H, m), 1.89 (3H, s), 4.55 (1H, m), 6.20 (1H, d), 6.68 (3H, m), 7.50 (1H, d, J=15.6 Hz), 7.65 (3H, m), 7.85 (1H, d), 8.40 (1H, bs), 8.60 (1H, d, J=5.8 Hz), 9.29 (1H, s); [M$^{+1}$] 449.7 (C$_{27}$H$_{26}$F$_2$N$_2$O$_2$ requires 448.51).

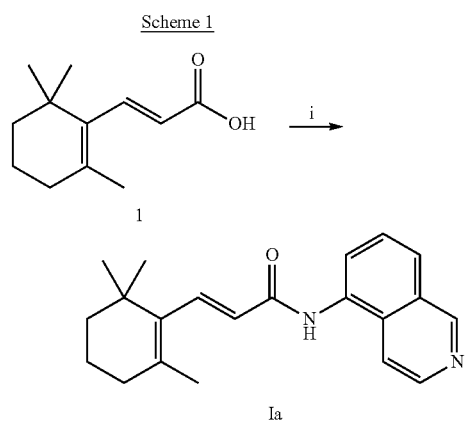

Scheme 1

Reagents:
i EDCl, HOBt, 5-aminoisoquinoline, DMF, rt

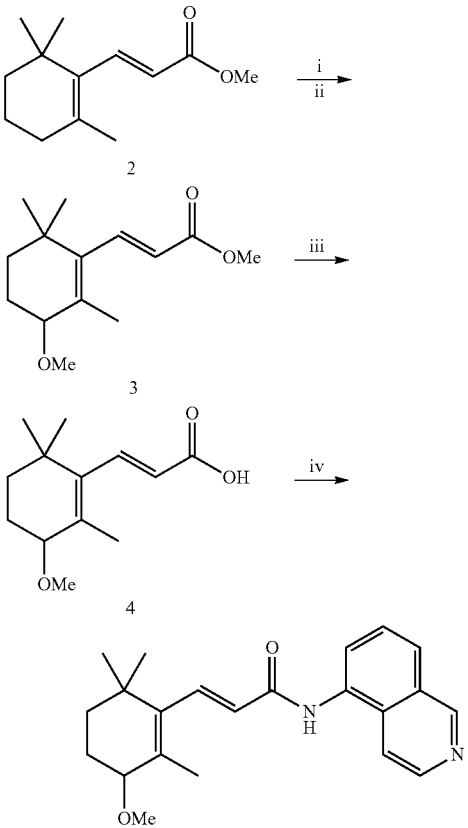

Scheme 2

Reagents:
i NBS/CCl$_4$
ii MeOH, Rfx;
iii LiOH, THF/MeOH/water, rt;
iv EDCl, HOBt, 5-aminoisoquinoline, DMf, rt Scheme 3

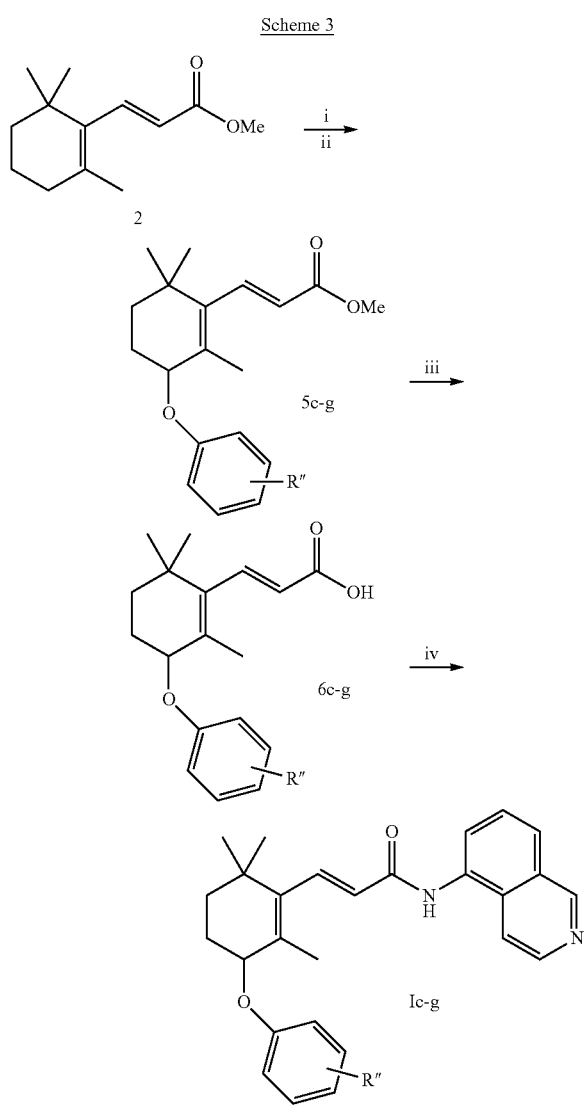

c: R″ = H
d: R″ = 4-chloro
e: R″ = 4-fluoro
f: R″ = 3-fluoro
g: R″ = 3,4-difluoro Reagents:
i NBS/CCl$_4$;
ii R″PhONa, EtOH, rt;
iii LiOH, THF/MeOH/water, rt;
iv EDCl, HOBt, 5-aminoisoquioline, DMF, rt Biological Assays Newborn and adult Sprague-Dawley rats (~250 g) were used (Harlam, Italy). All experiments complied with the national guidelines and were approved by the regional ethics committee.

Radioligand Binding Assay

Male Sprague-Dawley rats with body weight between 250 and 350 g at the time for testing were used. For binding assays rats were sacrificed by decapitation under anesthesia and the spinal cord was removed and disrupted using a Polytron tissue homogenizer in ice cold buffer containing 5 mM KCl, 5.8 mM NaCl, 0.75 mM CaCl$_2$, 2 mM MgCl$_2$, 320 mM sucrose, 10 mM Hepes, pH 8.6.[5] The homogenized tissue was centrifuged at 1000×g for 10 min at 4° C. and the supernatant was centrifuged again at 35000×g for 30 min at 4° C. (Beckman Avanti J25). The pellet was resuspended in the same buffer described above and used in binding experiments. In saturation experiments, 150 μg protein/sample from membrane suspensions were incubated with [$^3$H]-resiniferatoxin ([$^3$H]-RTX) (0.003-3 nM) in the assay buffer containing 0.25 mg/ml fatty acid-free bovine serum albumin at 37° C. for 60 min. In competition experiments, the membranes were incubated at 37° C. for 60 min with [$^3$H]RTX (0.4 nM) and increasing concentrations of the examined compounds in the range from 0.1 nM to 3 μM. Non-specific binding was defined in the presence of 1 μM RTX. After incubation, the reaction mixture was cooled at 0° C. and incubated with bovine α1-acid glycoprotein (200 μg per tube) for 15 min to reduce non-specific RTX binding. Membrane-bound RTX was separated from free RTX through centrifugation of the samples at 18500×g for 15 min. The tip of the microcentrifuge tube containing the pellet was cut off and radioactivity was determined by scintillation counting (Packard 2500 TR). Protein concentration was determined according to a Bio-Rad method with bovine serum albumin as reference standard (Bradford, 1976). Saturation and competition studies were analysed with the program Ligand.[6]

$Ca^{2+}$ Fluorescence Measurements in Cultured rat Trigeminal Ganglia

Two-days old Newborn rats were terminally anaesthetized and decapitated. Trigeminal ganglia were removed and rapidly placed in a cold phosphate buffered solution (PBS) before being transferred to collagenase/dispase (1 mg/ml dissolved in $Ca^{2+}$- $Mg^{2+}$-free PBS) for 35 min at 37° C.[7] After the enzymatic treatment the ganglia were rinsed three times with $Ca^{2+}$- $Mg^{2+}$-free PBS and then placed in 2 ml of cold DMEM supplemented with 10% fetal bovine serum (FBS, heat inactivated), 2 mM L-glutamine, 100 μ/ml penicillin and 100 μg/ml streptomycin. The ganglia were dissociated into single cells by several passages through a series of syringe needles (23G down to 25G). Finally, the medium and the ganglia cells were sieved through a 40 μm filter to remove debris and topped up with 8 ml of DMEM medium and centrifuged (200×g for 5 min). The final cell pellet was resuspended in DMEM medium [supplemented with 100 ng/ml mouse Nerve Growth Factor (mouse-NGF-7S) and cytosine-β-D-arabinofuranoside free base (ARA-C) 2.5 μM]. Cells were plated on poly-L-lysine-(8.3 μM) and laminin-(5 μM) coated 25 mm glass cover slips and kept for 5 to 8 days at 37° C. in a humidified incubator gassed with 5% $CO_2$ and air. Plated neurons were loaded with Fura-2-AM-ester (3 μM) in $Ca^{2+}$ buffer solution of the following composition (mM): CaCl$_2$ 1.4, KCl 5.4, MgSO$_4$ 0.4, NaCl 135, D-glucose 5, HEPES 10 with BSA (0.1%), at pH 7.4, for 40 min at 37° C. The plated neurons were then washed twice with the $Ca^{2+}$ buffer solution and transferred to a chamber on the stage of Nikon eclipse TE300 microscope. Fura-2-AM-ester was excited at 340 nM and 380 nM to indicate relative $[Ca^{2+}]_i$ changes by the $F_{340}/F_{380}$ ratio recorded with a dynamic image analysis system (Laboratory Automation 2.0, RCS, Florence, Italy). After transferring the plated neurons to the chamber, they were allowed (at least 10 min) to attain a stable fluorescence before beginning the experiment. A calibration curve was performed using buffer containing Fura-2-AM-ester and determinant concentrations of free $Ca^{2+}$. This curve was then used to convert the data obtained from $F_{340}/F_{380}$ ratio to $[Ca^{2+}]_i$ (nM).[8] The effects of pretreatments with capsazepine (CPZ), SB366791 and compounds of formula (I) on the increase in $[Ca^{2+}]_i$ produced by 0.1 μM capsaicin were studied.

Capsaicin-induced Secondary Allodynia in Rat

Capsaicin (20 nmols/50 µl/paw) was injected in the plantar surface of the glabrous skin of the right paw of rats anesthetized with diethyl ether (Chaplan et al., 1994). Compound Id was orally administered (10 mg/kg) 2 hours prior to capsaicin injection. Tactile allodynia was evaluated 90 min after capsaicin challenge.

Drugs and Reagents

Drugs and reagents were obtained from the indicated companies: [$^3$H]-Resiniferatoxin (Perkin Elmer, Boston, Mass.), SB-366791 (Tocris, UK), capsaicin, capsazepine, ionomycin, laminin, poly-L-lysine, substance P (Sigma, Italy); mouse NGF-7S and collagenase/dispase (Roche Diagnostics, Italy); Dulbecco's Modified Eagle's medium (DMEM), fetal bovine serum (FBS) heat inactivated, L-glutamine (200 mM), penicillin/streptomycin (10,000 IU/ml±10,000 UG/ml), (Gibco, Italy); Fura-2-AM-ester (Societa Italiana Chimici, Italy). Stock concentrations of capsaicin (10 mM), capsazepine (10 mM), SB-366791 (1 mM) and compounds of formula (I) were prepared in 50% DMSO and 50% Tween 80. Fura-2-AM-ester and ionomycin were dissolved in 100% DMSO. All the other drugs were dissolved in distilled water. Appropriate dilutions were then made in Krebs buffer solution.

Results

Radioligand Binding Assay

The saturation curve of [$^3$H]-RTX to TRPV1 expressed in rat spinal cord showed a $K_D$ value of 0.21 (0.16-0.27) and $B_{max}$ value of 57 (53-62) fmol/mg protein. The Scatchard plot was essentially linear and computer analysis of the data indicated that only one class of high affinity binding sites was present. Competition binding experiments of [$^3$H]-RTX revealed that compounds Ia, Ib, Ic, Id, Ie, If, Ig and reference compound (E)-3-(4-chlorophenyl)-N-3-methoxyphenyl) acrylamide (SB-366791) had a $K_i$ value of 66 (56-78) nM, 26.2 (21.1-32.6) nM, 4.93 (3.40-7.16) nM, 27 (23-32) nM, 14.8 (10.2-21.5) nM, 8.14 (6.87-9.65) nM, 10.3 (7.9-13.4) nM and 36 (30-43) nM respectively.

Ca$^{2+}$ Fluorescence

Capasaicin (0.1 µM) caused an increase in [Ca$^{2+}$] in the majority (95%) of rat trigeminal neurons cells, which were therefore identified as TRPV1 expressing neurons. IC$_{50}$ values of Ia, Ib, Ic, Id, Ie, If and Ig inhibiting capsaicin-evoked [Ca$^{2+}$]$_i$ mobilization were 44 (11-184) nM, 28.4 (25.2-31.9) nM, 2.12 (1.44-2.82) nM, 18.2 (4-98) nM, 5.25 (4.11-6.70) nM, 0.38 (0.36-0.40) and 0.65 (0.62-0.68) nM respectively. The reference TRPV1 antagonists, capsazepine, and SB-366791, inhibited the capsaicin response with an IC$_{50}$ of 948 (676-1330) nM and 8.7 (3.4-17.3) nM, respectively. The results are expressed as mean and 95% fiducial limits.

Capsaicin-induced Secondary Allodynia in Rat 90 min after the capsaicin challenge, compound Id showed a significant preventive effect (54%) against the pro-allodinic effect of capsaicin.

REFERENCES

1. Appendino, G. and Szallasi A. Progress in Medicinal Chemistry 2006, 44, 145-180.
2. Shimasaki, H.; Kagechika, H.; Fukasawa, H. Kawachi, E.; Shudo, K. Chemical & Pharmaceutical Bulletin 1995, 43, 100-7.
3. a) Baasov, T. and Sheves, M. Angew. Chem. 1984, 23, 803-804. b) Baraldi, P. G.; Pollini, G. P.; Simoni, D.; Zanirato, V.; Barco, A.; Benetti, S. Synthesis 1986, 9, 781-2.
4. Nanasawa, M. and Kamogawa, H. Bull. Chem. Soc. Jpn. 1982, 55, 3655-3656.
5. a) Szallasi A. and Blunberg P. M. Neurosciences 1992, 8, 368. b) Szallasi A. and Blunberg P. M. Naunyn Schmiedeberg's Arch Pharmacol. 1993, 347, 84-91.
6. Munson, P. J.; Rodbard, D. Anal. Biochem. 1980, 107, 220-239.
7. Rigoni, M.; Trevisani, M.; Gazzieri, D.; Nadaletto, R.; Tognetto, M.; Creminon, C.; Davis, J. B.; Campi, B.; Amatesi, S.; Geppetti, P.; Harrison, S. Br. J. Pharmacol. 2003, 138, 977-985.
8. Kudo, Y.; Ozaki, K.; Miyakawa, A.; Amano, T.; Ogura, A. Jap. J. Pharmacol. 1986, 41, 345-351.

The invention claimed is:

1. A compound of formula (I):

(I)

wherein:
Y is a group of formula

A

B

C in which:
R' is selected from hydrogen, halogen, hydroxy, (C$_1$-C$_6$) alkyl, (C$_2$-C$_6$)alkenyl, (C$_3$-C$_6$)alkynyl, (C$_1$-C$_6$) alkoxy, (C$_1$-C$_6$)alkylamino, phenyl, naphthyl, phenoxy, naphthoxy or phenylamino;

R is methyl or hydrogen;

n is 0 or 1;

X is selected from phenyl, pyridinyl, naphthyl, quinolinyl and isoquinolinyl; with the exclusion of the following compounds:

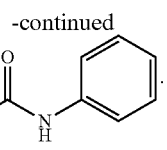

2. The compound according to claim 1, wherein n is 0 and X is 5-isoquinolinyl.

3. The compound according to claim 2, wherein R is hydrogen and Y is a group of formula:

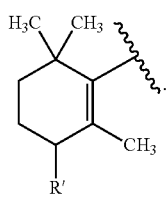

A

4. The compound according to claim 3, wherein R' is selected from the group consisting of hydrogen, methoxy or phenoxy.

5. A medicament comprising the compound of claim 1.

6. A pharmaceutical composition containing the compound of claim 1 in admixture with one or more carriers and/or excipients.

7. A method for preparation of analgesic medicaments, the method comprising admixing the compound of claim 1 with one or more carriers and/or excipients.

8. The compound of claim 1, wherein R' is an aromatic ring and the aromatic ring is substituted with one or more halogen, hydroxy, $(C_1-C_4)$alkyl, $(C_1-C_4)$alkoxy and trifluoromethyl groups.

9. The compound of claim 1, wherein X is substituted with one or more groups selected from halogen, hydroxy, $(C_1-C_4)$alkyl, $(C_1-C_4)$alkoxy and trifluoromethyl.

10. The compound of claim 3, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

11. The compound of claim 4, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

12. The medicament of claim 5, wherein the medicament is an analgesic medicament.

13. The pharmaceutical composition of claim 6, wherein in the compound of claim 1 n is 0 and X is 5-isoquinolinyl.

14. The pharmaceutical composition of claim 6, wherein in the compound of claim 1 R is hydrogen and Y is a group of formula:

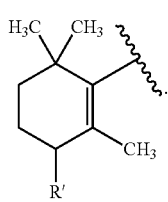

A

15. The pharmaceutical composition of claim 6, wherein in the compound of formula (I) R' is selected from the group consisting of hydrogen, methoxy or phenoxy.

16. The pharmaceutical composition of claim 6, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

17. The pharmaceutical composition of claim 6, wherein in the compound of formula (I) X is substituted with one or more groups selected from halogen, hydroxy, $(C_1-C_4)$alkyl, $(C_1-C_4)$alkoxy and trifluoromethyl.

18. The pharmaceutical composition of claim 14, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

19. The pharmaceutical composition of claim 15, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

20. A method for treating hyperalgesia in an individual, the method comprising administering to said individual a therapeutically effective amount of the compound of claim 1.

21. The method of claim 20, wherein in the compound of claim 1 n is 0 and X is 5-isoquinolinyl.

22. The method of claim 20, wherein in the compound of formula (I) R is hydrogen and Y is a group of formula:

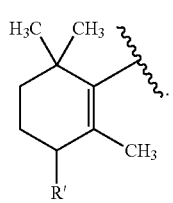

A

23. The method of claim 20, wherein in the compound of formula (I) R' is selected from the group consisting of hydrogen, methoxy or phenoxy.

24. The method of claim 20, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

25. The method of claim 20, wherein in the compound of formula (I) X is substituted with one or more groups selected from halogen, hydroxy, $(C_1-C_4)$alkyl, $(C_1-C_4)$alkoxy and trifluoromethyl.

26. The method of claim 22, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

27. The method of claim 23, wherein in the compound of formula (I) R' is an aromatic ring and the aromatic ring is substituted with one or more halogen, hydroxy, $(C_1-C_4)$alkyl, $(C_1-C_4)$alkoxy and trifluoromethyl groups.

* * * * *